US006372250B1

(12) United States Patent
Pardridge (10) Patent No.: US 6,372,250 B1
(45) Date of Patent: Apr. 16, 2002

(54) NON-INVASIVE GENE TARGETING TO THE BRAIN

(75) Inventor: William M. Pardridge, Pacific Palisades, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/557,349

(22) Filed: Apr. 25, 2000

(51) Int. Cl.$^7$ .................. A61K 9/127; A61K 48/00; C12N 15/88
(52) U.S. Cl. ................ 424/450; 435/458; 514/44
(58) Field of Search .................. 514/44; 424/450; 435/458

(56) References Cited

U.S. PATENT DOCUMENTS

| | | | |
|---|---|---|---|
| 5,154,924 A | 10/1992 | Friden | 424/179.1 |
| 5,182,107 A | 1/1993 | Friden | 424/179.1 |
| 5,672,683 A | 9/1997 | Friden et al. | 530/350 |
| 5,833,988 A | 11/1998 | Friden | 424/178.1 |
| 5,977,307 A | 11/1999 | Friden et al. | 530/350 |

OTHER PUBLICATIONS

P.A. Monnard et al., "Entrapment of Nucleic Acid in Liposomes," *Biochimica et Biophysica Acta* 1329 (1997) 39–50.
J. Huwyler et al., "Brain Drug Delivery of Small Molecules Using Immunoliposomes," *Proc. Natl. Acad. Sci. USA*, vol. 93, pp. 14164–14169, Nov. 1996, Neurobiology.
Verma et al. Nature 389:239–242 1997.*
Anderson Nature 392 Suppl:25–30 1998.*
Palu et al. J. Biotechnology 68:1–13 1999.*
Ishida et al. Nihon Rinshou 57(3):105–110 1998.*
Maruyama et al. J. Liposome Res. 8(1):81–82 1998.*
Fox, J.L. American Society for Microbiology News 66(2) Feb. 2000, web–based article.*

* cited by examiner

*Primary Examiner*—Robert A. Schwartzman
*Assistant Examiner*—Katharine F Davis
(74) *Attorney, Agent, or Firm*—Shapiro, Borenstein & Dupont LLP (57) ABSTRACT

Liposomes containing therapeutic genes are conjugated to multiple blood-brain barrier and brain cell membrane targeting agents to provide transport of the encapsulated gene across the blood-brain barrier and brain cell membrane. Once across the blood-brain barrier and brain cell membrane, the encapsulated gene expresses the encoded therapeutic agent within the brain to provide treatment and diagnosis of disease.

26 Claims, 5 Drawing Sheets

NON-INVASIVE GENE TARGETING TO THE BRAIN

BACKGROUND OF THE INVENTION

1. Field of the Invention

The present invention relates generally to the delivery of gene medicines to the brain. More particularly the present invention involves the combination of liposome technology, blood-brain barrier (BBB) receptor technology, pegylation technology, and therapeutic gene technology to provide formulations which are useful in the non-invasive delivery of genes to the brain.

2. Description of Related Art

The publications and other reference materials referred to herein to describe the background of the invention and to provide additional detail regarding its practice are hereby incorporated by reference. For convenience, the reference materials are numerically referenced and grouped in the appended bibliography.

The expression of exogenously administering genes in brain has previously been achieved in vivo with either viral vectors or cationic liposomes (1–4). However, in either case, highly invasive routes of administration are required. Such invasive techniques are needed because of the failure of either viruses or cationic liposomes to cross the brain capillary wall, which forms the blood-brain barrier (BBB) in vivo. The existence of the BBB necessitates the administration of the exogenous gene either intracerebrally via craniotomy (1), or by the intra-carotid arterial infusion of noxious agents that cause BBB disruption and transient opening of the BBB (4).

Human gene therapy of the brain will likely require repeated administration of the gene medicine. Therefore, it would be advantageous to administer the gene by a route that is no more invasive than a simple intravenous injection. With this approach, the gene therapeutic is delivered through the BBB by targeting the gene medicine to the brain via endogenous BBB transport systems (5). Carrier-mediated transport (CMT) systems exist for the transport of nutrients across the BBB (5). Similarly, receptor-mediated transcytosis (RMT) systems operate to transport circulating peptides across the BBB, such as insulin, transferrin, or insulin-like growth factors (5). These endogenous peptides can act as "transporting peptides," or "molecular Trojan horses," to ferry drugs across the BBB. In this approach, called the chimeric peptide technology, the drug that is normally not transported across the BBB is conjugated to a "transportable peptide, and the drug/transportable peptide conjugate undergoes RMT through the BBB (U.S. Pat. No. 4,801,575).

Peptidomimetic monoclonal antibodies (MAb) that bind endogenous transport systems within the BBB, such as the transferrin receptor (TfR) or insulin receptor, have been used in previous studies for targeting neuropeptides or antisense agents through the BBB in vivo (5). The ability of certain receptor-binding MAbs to mimic the action of the endogenous peptide that binds the same receptor is well known in the literature (35–37). In addition, the ability of such peptidomimetic MAbs, such as anti-TfR MAbs, to transport drugs into cells via these receptor-mediated endocytosis is also well known (38).

The expression in the brain of a therapeutic gene requires that the gene formulation that is injected into the blood is transported not only across the BBB by RMT, but also across the brain cell membrane (BCM) by receptor-mediated endocytosis (RME) into the target cell in brain. In addition, using endogenous BBB transport systems to target gene medicines non-invasively to the brain also requires the development of a suitable formulation of the gene therapeutic that is stable in the bloodstream. Cationic liposome/DNA complexes have been used for in vivo gene expression, but these formulations aggregate extensively in saline solution (6–11). This aggregation results in selective gene expression in the lung with little expression in peripheral tissues (12–14), and no expression in brain following intravenous administration of the cationic liposome/DNA complex (12). The DNA plasmid could be conjugated to the peptidomimetic MAb via a cationic polylysine bridge (15–17). However, electrostatic interactions between DNA and polycations may not be stable in blood, and highly polycationic proteins such as histone or polylysine exert toxic effects at the BBB and cause generalized BBB permeability changes in vivo (18).

SUMMARY OF THE INVENTION

In accordance with the present invention, therapeutic genes are introduced non-invasively into the brain across the blood brain barrier. Once inside the brain, the therapeutic genes express therapeutic agents which are useful in the diagnosis and treatment of brain disease. The present invention is based on the use of liposomes which are capable of delivering therapeutic genes across the blood-brain barrier.

The liposomes of the present invention include a neutral liposome having an exterior surface and an internal compartment in which the therapeutic gene is located. The surface of the liposome is decorated with several thousand strands of polyethyleneglycol (PEG), a process called "pegylation." The PEG strands make the surface of the liposome "hairy," and this prevents the rapid absorption of blood proteins to the surface of the liposome, which is what accelerates the rapid removal from blood of unprotected liposomes. In contrast, the pegylated liposomes are protected and are removed from blood at a much slower rate. The PEG strands also act as "conjugation agents" for attachment of the "transportable peptide" to the surface of the pegylated liposome, which is what triggers the RMT of the complex through the BBB and the RME through the BCM in vivo. The therapeutic gene includes a sufficient amount of DNA to encode a therapeutic agent. A plurality of blood-brain barrier targeting agents are attached to the liposome surface via a conjugation agent. The therapeutic gene located within the immunoliposome targeting vehicle is transported across the blood-brain barrier and released into the interstitial space of brain. Once there, the "pegylated liposome" undergoes receptor-mediated endocytosis into target cells in brain because the surface of the liposome is decorated with "transportable peptides" that recognize receptor located on the brain cell plasma membrane (BCM). Owing to the presence of insulin or transferrin receptors on both the BBB and the BCM, the "transportable peptide" catalyzes transport across both of the 2 barriers in brain: the BBB and the BCM. Once inside the target brain cell, the liposome complex is entrapped within brain cell endosomes, followed by release of the gene therapeutic into the ctoplasm of brain cells, where it can enter the nucleus, resulting in expression of the therapeutic agent.

It was found in accordance with the present invention that the use of liposomes in which the polyethyleneglycol is conjugated to the liposome surface results in an increase in the plasma bioavailability of the DNA incorporated within the interior of the immunoliposome. It was also found that the stability of the DNA located within the immunoliposome is increased during in vivo use. Further, in addition to achieving expression of an exogenous gene in the brain, it is also possible to achieve, in parallel, gene expression in other organs which contain or express high levels of the receptor targeted by the blood-brain barrier targeting agent.

The above described and many other features and attendant advantages of the present invention will become better understood by reference to the following detailed description when taken in conjunction with the accompanying drawings.

BRIEF DESCRIPTION OF THE DRAWINGS

FIG. 1A is a diagrammatic representation of a preferred exemplary embodiment in which a pGL2 luciferase expression plasmid is encapsulated in an OX26 (BBB targeting agent) pegylated immunoliposomes constructed from neutral lipids. There are approximately 3000 strands of polyethylene glycol of 2000 Daltons molecular weight, designated $PEG^{2000}$, attached to the liposome surface, and about 1% of the PEG strands is conjugated with the OX26 monoclonal antibody to the rat transferrin receptor. The OX26 MAb is a peptidomimetic MAb and undergoes RMT through the BBB on the endogenous pathway that mediates BBB transport of the transferrin (5).

FIG. 1B is a graph showing that the mean diameter of the pegylated liposomes encapsulating the pGL2 plasmid DNA is 73 nm.

FIG. 1C shows electrophoresis of liposomes before (lane 2) and after (lane 1) DNAse1/exonuclease III treatment. The electrophoresis was conducted in 0.8% agarose gel electrophoresis followed by ethidium bromide (Et Br) staining. DNA molecular weight size standards are shown in the left hand side. Approximately 50% of the DNA associated with the pegylated liposome was bound to the exterior of the liposome (lane 2) and this was quantitatively removed by the nuclease treatment (lane 1). A trace amount of the pGL2 plasmid was radiolabeled with $^{32}P$ and film autoradiography of the gel showed a single 5.8 kb band with no low molecular weight radiolabeled DNA. These results show that all of the DNA is packaged in the interior of the pegylated immunoliposome.

In FIG. 1D, the conjugation of the OX26 MAb to the pegylated liposomes carrying the encapsulated pGL2 plasmid following nuclease digestion is demonstrated by Sepharose CL-4B gel filtration chromatography. A trace amount of the encapsulated pGL2 plasmid DNA was labeled with $^{32}P$ and a trace amount of the OX26 MAb was radiolabeled with $^3H$. This shows the co-migration of the conjugated OX26 MAb and the encapsulated pGL2 plasmid DNA.

FIG. 5D shows the lumen (L) of a capillary of the choroid plexus, and FIG. 5E shows the thalamic (thal) nuclei below the choroid plexus of the third ventricle, which is also visible in FIG. 5A.

DETAILED DESCRIPTION OF THE INVENTION

The immunoliposomes in accordance with the present invention are designed for delivering therapeutic genes across the blood-brain barrier followed by expression in the brain of the therapeutic agents encoded by the gene. The liposomes are a form of nanocontainer and nanocontainers, such as nanoparticles or liposomes, are commonly used for encapsulation of drugs. The liposomes preferably have diameters of less than 200 nanometers. Liposomes having diameters of between 50 and 150 nanometers are preferred. Especially preferred are liposomes or other nanocontainers having external diameters of about 80 nanometers. Suitable types of liposomes are made with neutral phospholipids such as 1-palmitoyl-2-oleoyl-sn-glycerol-3-phosphocholine (POPC), diphosphatidy phosphocholine, distearoylphosphatidylethanolamine (DSPE), or cholesterol, along with a small amount (1%) of cationic lipid, such as didodecyldimethylammonium bromide (DDAB) to stabilize the anionic DNA within the liposome.

The therapeutic gene which is encapsulated within the liposome can be any of the common therapeutic genes which are used to express therapeutic and diagnostic agents. Exemplary therapeutic genes include brain-derived neurotrophic factor (BDNF) for treatment of neurodegenerative disease, stroke, or brain trauma; tyrosine hydroxylase and/or aromatic amino acid decarboxylase for Parkinson's disease; β-glucuronidase; hexosaminidase A; herpes simplex virus thymidine kinase or genes encoding antisense RNA to the epidemal growth factor receptor for treatment of brain tumors; lysosomal storage disorder replacement enzymes for Tay-Sachs and other lysosomal storage disorders; gene encoding antisense RNA for the treatment of the cerebral component of acquired immune deficiency syndrome (AIDS). In addition to the therapeutic gene, the plasmid DNA may also contain DNA sequences either before or after the therapeutic sequence and these additional parts of the plasmid may promote tissue-specific transcription of the plasmid in a particular cell in the brain, may promote enhanced translation and/or stabilization of the mRNA of the therapeutic gene, and may enable episomal replication of the transgene in brain cells. In general, the therapeutic gene will contain at least 100 nucleotides or have a molecular weight above 30,000 Daltons. It is preferred that the therapeutic gene be contained within a plasmid or other suitable carrier for encapsulation within the internal compartment of the liposome or nanocontainer.

The therapeutic gene may be encapsulated within the liposome according to any of the well known drug encapsulation processes. For example, encapsulation by sonication, freeze/thaw, evaporation, and extrusion through membrane filters.

The number of therapeutic genes encapsulated within the liposome may vary from 1 to many, depending on the disease being treated. The limiting factor will be the diameter of therapeutic gene that is encapsulated within the liposome. Using polycationic proteins such as histone, protamine, or polylysine, it is possible to compact the size of plasmid DNA that contains several thousand nucleotides to a structure that has a diameter of 10–30 nm. The volume of a 100 diameter liposome is 1000-fold and 35-fold greater than the volume of a 10 nm and 30 nm DNA compacted sphere, respectively. Therefore, it is possible to encapsulate many copies of the same gene or multiple copies of multiple genes within the liposome.

In order to provide transport of the encapsulated therapeutic gene across the blood-brain barrier, a number of blood-brain targeting agents are conjugated to the surface of the liposome. Suitable targeting agents include insulin, transferrin, insulin-like growth factor, or leptin, as these peptides all have endogenous RMT systems within the BBB that also exist on the BCM, and these endogenous peptides could be used as "transportable peptides." Alternatively, the surface of the liposome could be conjugated with 2 different "transportable peptides," one peptide targeting an endogenous BBB receptor and the other targeting an endogenous BCM peptide. The latter could be specific for particular cells within the brain, such as neurons, glial cells, pericytes, smooth muscle cells, or microglia. Targeting peptides may be endogenous peptide ligands of the receptors, analogues of the endogenous ligand, or peptidomimetic MAbs that bind the same receptor of the endogenous ligand. The use of transferrin receptor (TfR)-specific peptidomimetic monoclonal antibodies as BBB "transportable peptides" are described in detail in U.S, Pat. Nos. 5,154,924; 5,182,107; 5,527,527; 5,672,683; 5,833,988; and 5,977,307. The use of an MAb to the human insulin receptor (HIR) as a BBB "transportable peptide" has been described (33).

The conjugation agents which are used to conjugate the blood-barrier targeting agents to the surface of the liposome can be any of the well-known polymeric conjugation agents such as sphingomyelin, polyethylene glycol (PEG) or other organic polymers. PEG is an especially preferred conjugation agent. The molecular weight of the conjugation agent is preferably between 1000 and 50,000 DA. A particularly preferred conjugation agent is a bifunctional 2000 DA PEG which contains a lipid at one end and a maleimide group at the other end. The lipid end of the PEG binds to the surface of the liposome with the maleimide group bonding to the receptor-specific monoclonal antibody or other blood-brain barrier targeting vehicle. It is preferred that from 5 to 1000 targeting vehicles be conjugated to each liposome. Liposomes having approximately 25–40 targeting vehicles conjugated thereto are particularly preferred.

Exemplary combinations of liposomes, conjugation agents and targeting agents are as follows:

A transportable peptide such as insulin or an HIRMAb is thiolated and conjugated to a maleimide group on the tip of a small fraction of the PEG strands; or, surface carboxyl groups on a transportable peptide such as transferrin or a TfRMAb are conjugated to a hydrazide (Hz) moiety on the tip of the PEG strand with a carboxyl activator group such as N-methyl-N'-3(dimethylaminopropyl)carbodiimide hydrochloride (EDAC); a transportable peptide is thiolated and conjugated via a disulfide linker to the liposome that has been reacted with N-succinimidyl 3-(2-pyridylthio) proprionate (SPDP); or a transportable peptide is conjugated to the surface of the liposome with avidin-biotin technology, e.g., the transportable peptide is mono-biotinylated and is bound to avidin or streptavidin (SA), which is attached to the surface of the PEG strand.

Figure 4:
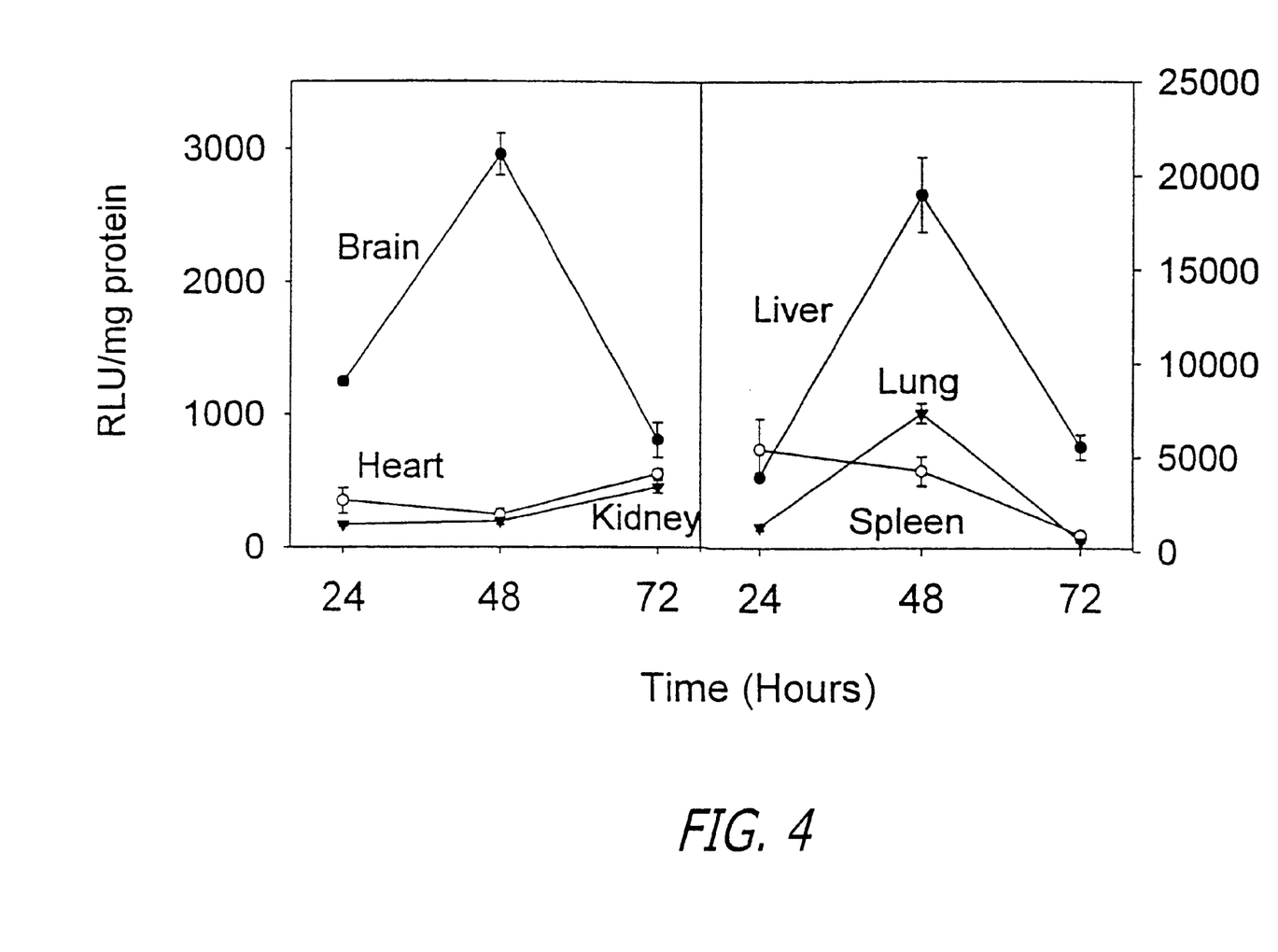
FIG. 4 depicts graphs showing the organ luciferase activity, expressed as relative light units (RLU) per mg tissue protein, for brain, heart, kidney, liver, lung, and spleen at 24, 48, and 72 hours after injection of the pGL2 plasmid DNA encapsulated in pegylated immunoliposomes that are conjugated with the OX26 MAb in accordance with the present invention. Data are mean ±SE (n=3 rats/group).
Figure 5A:
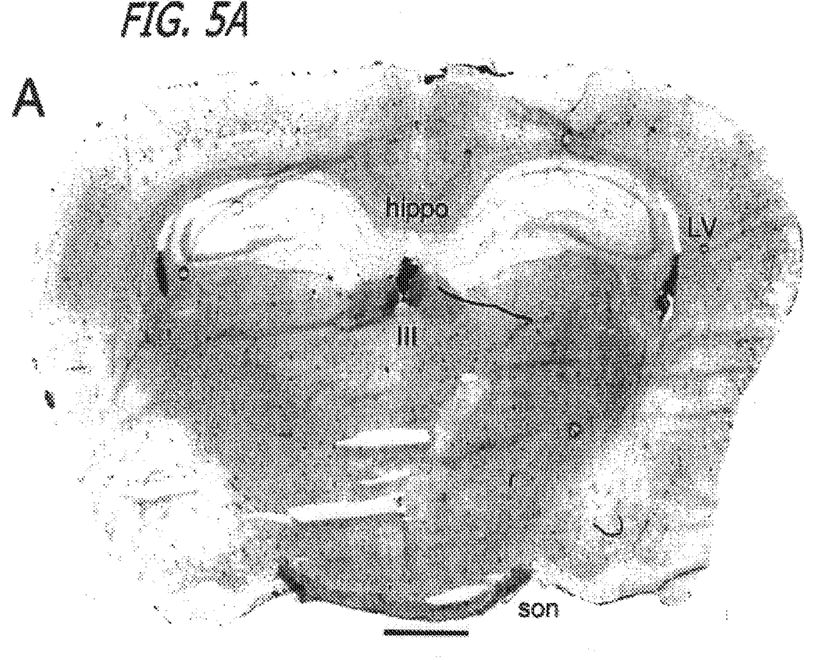
FIGS. 5A–F are photographs showing β-galactoside histochemistry in brain (FIGS. 5A–E) and liver (FIG. 5F) at 48 hours after intravenous injection of the β-galactoside gene packaged inside the OX26 pegylated immunoliposome in accordance with the present invention (FIGS. 5B–F). The control brain from rats receiving no gene administration is shown in FIG. 5B. Magnification=1.5 mm (FIG. 5A), 2.2 mm (FIG. 5B), 57 μm (FIG. 5C), 23 μm (FIG. 5D), 230 μm (FIG. 5E), and 15 μm (FIG. 5F). FIGS. A and B are not counter-stained. The lateral ventricles (LV), third ventricle (III), left or right hippocampus (hippo), and hypothalamic supraoptic nuclei (son) are labeled in FIG. 5A.
Figure 5B:
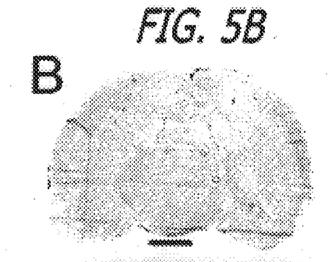
Figure 5C:
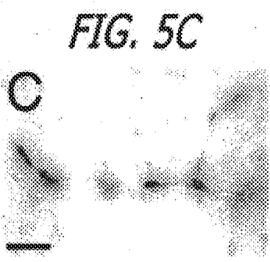
Figure 5D:
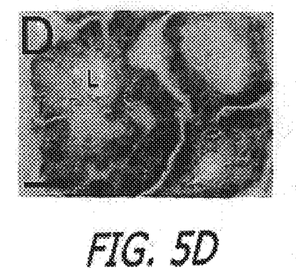
Figure 5E:
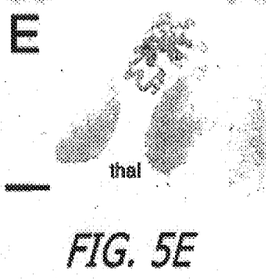
Figure 5F:
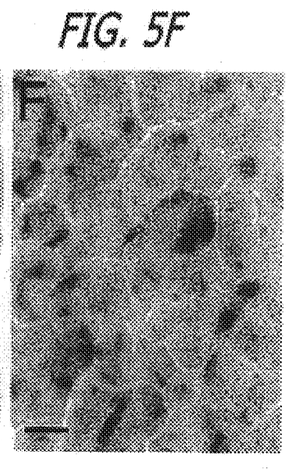

Although the invention has been described using liposomes as the preferred nanocontainer, it will be recognized by those skilled in the art that other nanocontainers may be used. For example, the liposome can be replaced with a nanoparticle or any other molecular nanocontainer with a diameter <200 nm that can encapsulate the DNA and protect the nucleic acid from nucleases while the formulation is still in the blood or in transit from the blood to the intracellular compartment of the target cell. Also, the PEG strands can be replaced with multiple other polymeric substances such as sphingomylein, which are attached to the surface of the liposome or nanocontainer and serve the dual purpose of providing a scaffold for conjugation of the "transportable peptide" and for delaying the removal of the formulation from blood and optimizing the plasma pharmacokinetics. Further, the present invention contemplates delivery of genes to any group of cells or organs which have specific target receptors. As shown in FIG. 4, the present application may be used to deliver genes to organs, such as liver, lung and spleen.

The immunoliposomes in accordance with the present invention may be combined with any suitable pharmaceutical carrier for intravenous administration. Intravenous administration of the immunoliposome is the preferred route since it is the least invasive. Other routes of administration are possible, if desired. Suitable pharmaceutically acceptable carriers include saline, Tris buffer, phosphate buffer, or any other aqueous solution.

A therapeutically effective amount of the immunoliposome will vary widely depending upon the individual being treated and the particular gene being administered. The appropriate dose will be established by procedures well known to those of ordinary skill in the art.

Examples of Practice

The following examples of the present invention describe an exogenous plasmid DNA, wherein either a $\beta$-galactosidase or a luciferase expression plasmid, driven by the SV40 promoter, is incorporated in the interior of neutral liposomes that are pegylated with PEG of 2000 Daltons molecular weight, designated $PEG^{2000}$. Approximately 40 of the PEG strands per liposome are tethered with the OX26 murine MAb to the rat transferrin receptor. The OX26 MAb, or transferrin, undergo receptor-mediated transcytosis through the BBB in vivo. The property of a peptidomimetic MAb, such as OX26, enables brain targeting of the pegylated immunoliposomes by triggering transport into brain via the BBB TfR.

Materials. POPC (1-palmitoyl-2-oleoyl-sn-glycerol-3-phosphocholine) and DDAB (didodecyldimethylammonium bromide) were purchased from Avanti Polar Lipids Inc. (Alabaster, Ala.). DSPE (distearoylphosphatidylethanolamine)-$PEG^{2000}$-maleimide was custom-synthesized by Shearwater Polymers. [α-$^{32}$P] dCTP (800 Ci/mmol) was from NEN Research Products (Boston, Mass.). $^{125}$NaI and N-succinimidyl[2,3-$^3$] propionate ($^3$H-NSP) as from Amersham LIFE SCIENCE (Arlington Height, Ill.). The nick translation system was purchased from GIBCO BRL (Fredrick, Md.). Pancreatic Dnase I (from bovine pancreases), with a specific activity of 2000 Kunitz units/mg was purchased from Sigma Chemicals (St. Louis, Mo.). Luciferase reagent, recombinant luciferase, the 6.8 kb pSV-β-galactosidase plasmid, and exonuclease III were obtained from Promega (Madison, Wis.). Protein G Sepharose CL-4B was from Pharmacia Biotech Inc. (Piscataway, N.J.). Mouse myeloma ascites IgG2a (κ) was from Cappel (Westchester, Calif.). Centriprep-30 (molecular weight cutoff: 30,000) concentrator was obtained from Amicon (Beverly, Mass.). Male Sprague Dawley rats (weighing from 200–250 g) were obtained from Harlan (Indianapolis, Ind.).

Plasmid Production. The 5.8 kb plasmid, pGL$_2$, encoding for the firefly *Photinus pyralis* luciferase gene, or the 6.8 kb pSV-β-galactosidase plasmid, both under the influence of the SV40 promoter, were obtained from Promega. The plasmids were amplified in the JM 109 strain of *Escherichia coli*. DNA was extracted using alkaline lysis method and purified by precipitation with isopropanol, using Q1Afilter Plasmid Maxi kit (QIAGEN, Valencia, Calif.). DNA was measured by UV absorption at 260 nm and dissolved in TE buffer. Linearized DNA was obtained by digestion with BamHI. Its size was confirmed by 0.8% agarose gel electrophoresis and ethidium bromide staining.

DNA radiolabeling. Supercoiled DNA was labeled with [α-$^{32}$P]dCTP by the nick translation method (Nick Translation System, Promega), using DNA polymerase I and Dnase I. Unincorporated nucleotide was removed by a G25 Sephadex column (Boehringer Mannheim, Ind.). The specific activity of the labeled probe is 5×10$^6$ cpm/μg.

The linearized plasmid was $^{32}$P-radiolabeled at both 5' and 3' ends with T4 polymerase and purified with a Sephadex G-25 spin column to a trichloroacetic acid (TCA) precipitability of 98%. This material was analyzed with 0.8% agarose gel electrophoresis and film autoradiography and migrated as a single band of 5.8 kb with no low molecular weight radiolabeled impurities.

The $^{32}$P-linearized plasmid was used in the pharmacokinetic experiments. The $^{32}$P-supercoil plasmid was used as a tracer to measure the incorporation of the unlabeled supercoil plasmid in the liposomes.

Pegylated Liposome synthesis and plasmid DNA encapsulation. POPC (19.2 μmol), DDAB (0.2 μmol), DSPE-PEG$^{2000}$ (0.6 μmol), and DSPE-PEG$^{2000}$-maleimide (30 nmol) were dissolved in chloroform/methanol (2:1, vol:vol) followed by evaporation. The lipids were dispersed in 1 ml 0.05 M Tris-Cl buffer (pH=8.0) and sonicated for 10 minutes (20). Supercoiled DNA (100 μg) and 1 μCi $^{32}$P-DNA were added to the lipids. The liposomes/DNA dispersion was evaporated to a final concentration of 200 mM at a volume of 100 μl. The dispersion was frozen in ethanol/dry ice for 4–5 minutes and thawed at 40° C. for 1–2 minutes, and this freeze-thaw cycle was repeated 10 times. The liposome dispersion was diluted to a lipid concentration of 40 mM followed by extrusion 10 times each through 2 stacks each of 400 nm, 200 nm, 100 nm, and 50 nm pore size polycarbonate membranes, using a hand held extruder (Avestin, Ottawa, Canada), as described previously (19). The mean vesicle diameters were determined by quasielastic light scattering using a Microtrac Ultrafine Particle Analyzer (Leeds-Northrup, St. Petersburg, Fla.), as described previously (19).

The plasmid absorbed to the exterior of the liposomes was removed by nuclease digestion (20). For digestion of the unencapsulated DNA, 5 U of pancreatic endonuclease I and 5 U of exonuclease III were added in 5 mM MgCl$_2$ and 0.1 mM of DTT to the liposome/DNA mixture after extrusion. After incubation at 37° C. for 1 hour, the reaction was stopped by adding 7 mM EDTA. The extent to which the nuclease digestion removed the exteriorized plasmid DNA was determined by agarose gel electrophoresis and ethidium bromide staining of aliquots taken before and after nuclease treatment.

Conjugation of OX26 MAb or mouse IgG2a to the pegylated liposome/DNA. The anti-rat transferrin receptor OX26 mAb was harvested from serum free OX26 hybridoma conditioned media as described (21). OX26 as well as the isotype control, mouse IgG2a, were purified by protein G Sepharose affinity chromatography (21). OX26 was radiolabeled with $^3$H-NSP as described previously (22). The $^3$H-OX26 had a specific activity of 0.13 μCi/μg and a TCA precipitability of 95%.

The OX26 or mouse IgG2a (1.5 mg, 10 nmol) was thiolated using a 40:1 molar excess of 2-iminothiolane (Traut's reagent), as described previously (19). The number of OX26 molecules conjugated per liposome was calculated from the total OX26 cpm in the liposome pool and the specific activity of the labeled OX26 MAb, assuming 100,000 lipid molecules per liposome, as described previously (19). The final % entrapment of the 100 μg pGL2 in the liposome preparation was computed from the $^{32}$P radioactivity, and was typically 30% or 30 μg plasmid DNA. This was then administered to 3 rats at a dose of 10 μg plasmid DNA per rat for luciferase gene expression measurements.

Pharmacokinetics. A pharmacokinetic study was performed in ketamine/xylazine anesthetized male Sprague Dawley rats, as described previously (19). The $^{32}$P-pGL2 (1 μCi) was injected in one of the following 3 formulations: (a) naked DNA, (b) DNA encapsulated in pegylated liposomes without antibody attached, or (c) DNA encapsulated in pegylated liposomes with OX26 MAb conjugated to the PEG strands.

Luciferase gene expression in vivo. The pegylated liposome/luciferase DNA, that was conjugated with either OX26 MAb or mouse IgG2a, was injected intravenously in anesthetized rats at a dose of 10 μg pGL2 DNA per rat. Rats were sacrificed at 24, 48 or 72 hours after injection. The brain, heart, kidney, spleen, liver and lung tissues were homogenized in 4 volumes of lysis buffer containing 0.1 M potassium phosphate buffer, pH 7.8, 1% Triton X-100, 1 mM dithiothreitol and 2 mM EDTA using a Polytron homogenizer. The homogenate was centrifuged at 14,000 rpm for 10 minutes at 4° C. The supernatant was used for measurement of tissue luciferase activity with a Luminometer (Biolumat LB 9507, Berthold, Nashua, N.H.); 100 μl of reconstituted luciferase substrate was added to 20 μl of tissue extract. Peak light emission was measured for 10 seconds at 20° C., and recorded as relative light units (RLU), as described previously (23). The background level was determined by measuring a sample containing only lysis buffer. The protein concentration in the tissue extract was determined with the bicinchoninic acid (BCA) protein assay reagent (Pierce, Rockford, Ill.).

β-Galactoside gene expression in vivo. The pegylated immunoliposome/β-galactosidase DNA was prepared exactly as described above with the OX26 MAb, and injected intravenously in rats as described above at a dose of 50 μg plasmid DNA per 0.25 kg adult rat. At 48 hours later, the brain and liver were removed, and rapidly frozen in powdered dry ice, dipped in Tissue-Tek OCT embedding medium, and 15 micron frozen sections were prepared on a Bright cryostat. The sections were fixed for 5 min at room temperature in 0.5% glutaraldehyde in 0.1 M $NaH_2PO_4$, and stored at −70 degrees, until β-galactosidase histochemistry with 5-bromo4-chloro-3-indoyl-β-D-galactose (X-gal, Promega), as described by the manufacturer. Slides were developed overnight at 37° C., and some slides were counter-stained with Mayer's hematoxylin. The slides were photographed or scanned with a 1200 dpi UMAX flatbed scanner with transilluminator, and cropped with Adobe Photoshop 5.5 with a G4 Power Macintosh.

Results

Figure 1:
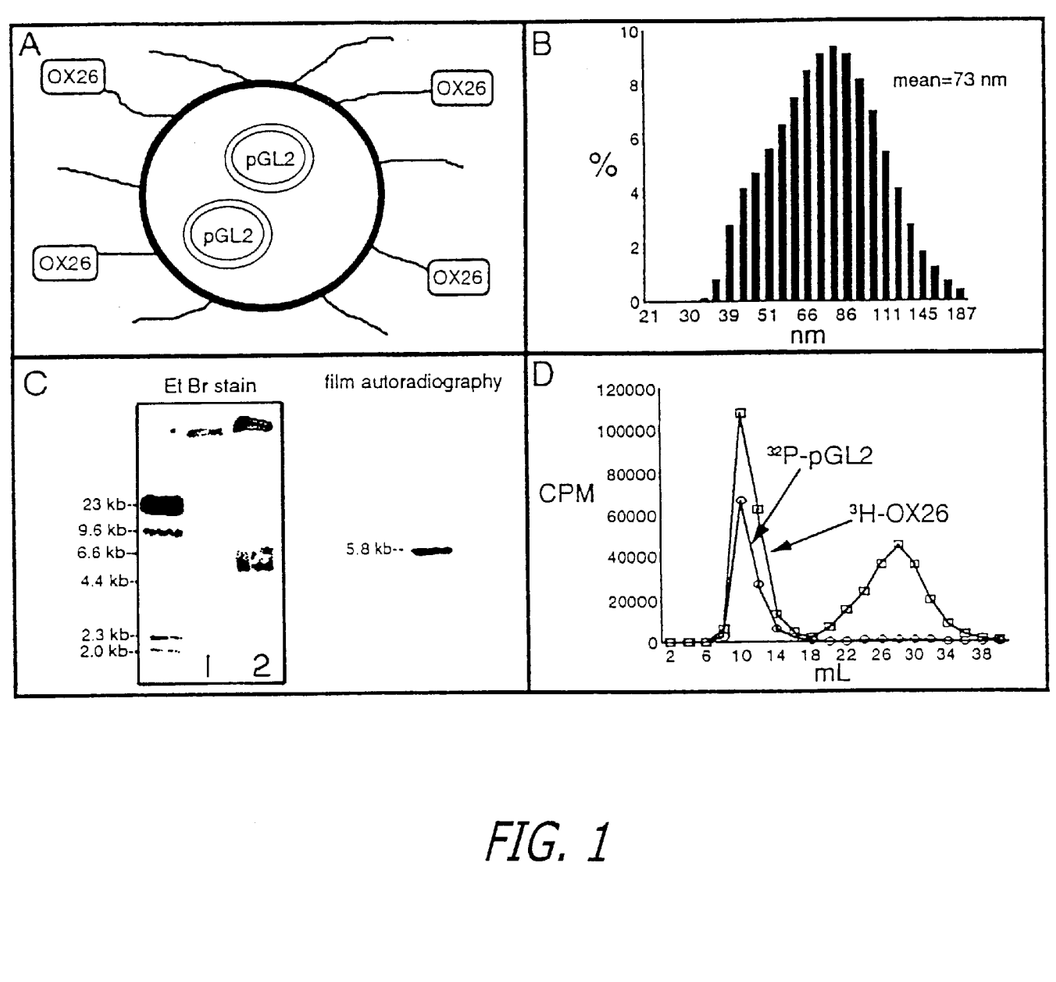

The structure of the pegylated immunoliposome carrying the pGL2 luciferase plasmid within the interior of the liposome is shown in FIG. 1A. The liposomes are formed in aqueous solution, as the mean diameter of the pegylated immunoliposomes carrying the pGL2 plasmid in the interior is 73 nm (FIG. 1b). During the formulation of the pegylated immunoliposome carrying the plasmid DNA, the complex is treated with a mixture of nucleases (Methods). This nuclease treatment removes any plasmid DNA bound to the exterior of the pegylated liposome; ethidium bromide staining following agarose gel electrophoresis demonstrates complete removal of any exterior bound plasmid from the preparation (FIGS. 1C, lane 1). When the pGL2 plasmid DNA was radiolabeled with $^{32}P$ prior to incorporation into the liposomes, only the 5.8 kb pGL2 plasmid was detected, and no low molecular weight forms of DNA were observed (FIG. 1C, film autoradiography). The covalent conjugation of the OX26 MAb to the tips of the PEG strands on the pegylated immunoliposome was monitored by Sepharose CL-4B gel filtration chromatography (FIG. 1D). These studies show co-migration of the $^{32}P$-pGL2 incorporated in the interior of the liposome with the $^{3}H$-labeled OX26 MAb attached to the PEG strands. Based on the specific activity of the OX26, it was calculated that this preparation of pegylated immunoliposome contained 39 molecules of OX26 MAb conjugated to the individual liposome.

Figure 2:
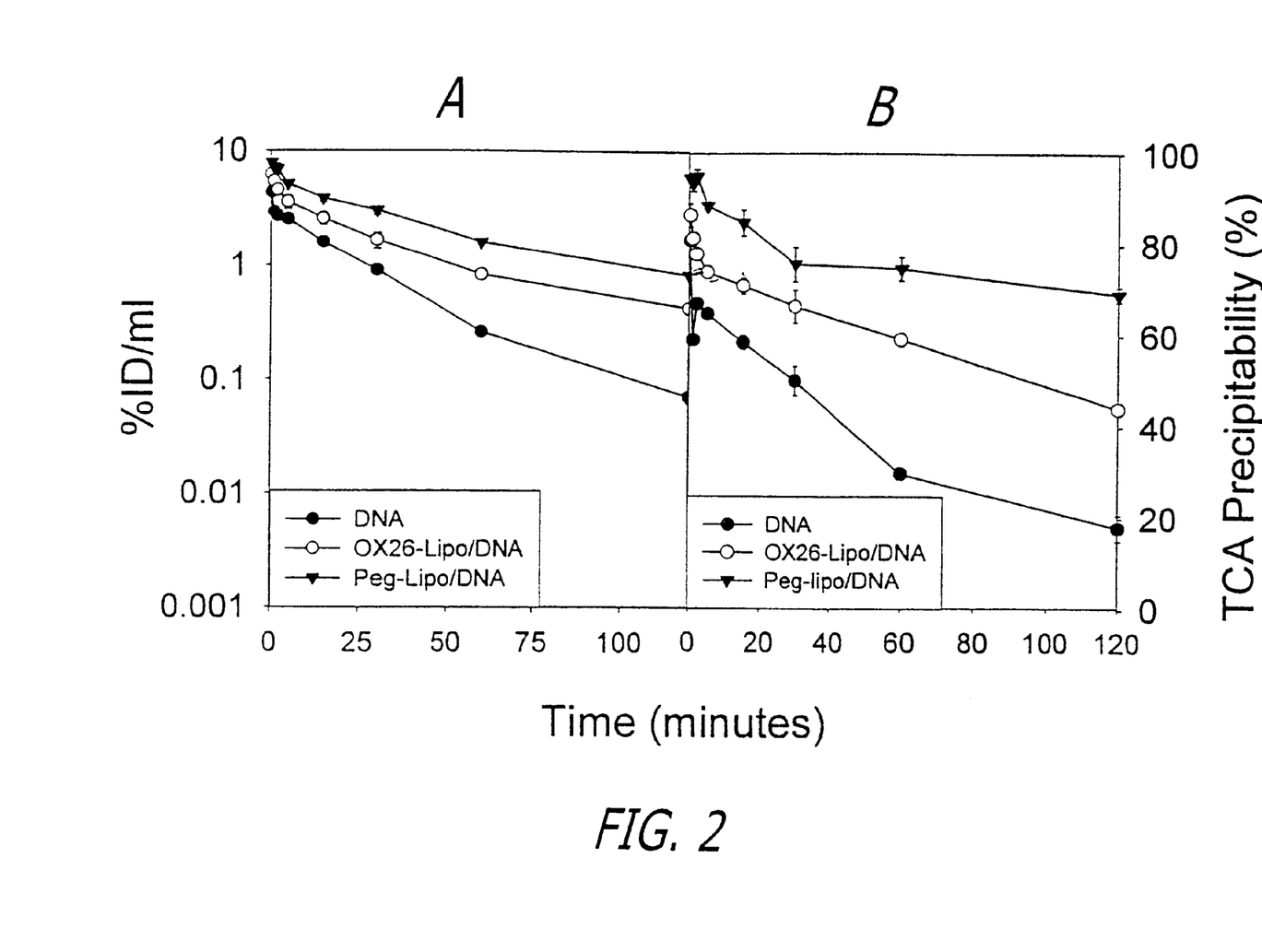
FIG. 2A shows a graph in which the percent of injected dose (ID) per mL plasma that is precipitated by trichloroacetic acid (TCA) is plotted versus the time after intravenous injection of the $^{32}P$ DNA in anesthetized rats for up to 120 minutes. The DNA was injected 1 of 3 formulations: (a) "naked" DNA (DNA), (b) pGL2 plasmid DNA encapsulated within the interior of nuclease treated OX26 pegylated immunoliposomes (OX26-Lipo/DNA), and (c) pGL2 plasmid DNA encapsulated in the interior of nuclease treated pegylated liposomes without OX26 MAb attached (Peg-Lipo/DNA).
FIG. 2B is a graph showing the percent of plasma radioactivity that is precipitated by TCA. Data mean are ±SE (n=3 rats/group).

The pharmacokinetic studies were performed with the linearized pGL2 plasmid DNA, which was end labeled with $^{32}P$. This was then injected into anesthetized rats in 1 of 3 forms: (a) naked DNA, (b) $^{32}P$-pGL2 plasmid incorporated in the interior of pegylated liposomes conjugated with no MAb, and (c) $^{32}P$-pGL2 plasmid DNA incorporated into the interior of pegylated immunoliposomes conjugated with OX26. These 3 different preparations were each injected into different groups of rats and the plasma radioactivity that was precipitated with trichlororacetic acid (TCA) was determined at various times up to 2 hours after intravenous administration (FIG. 2, right panel). The naked DNA was rapidly removed from the plasma with a clearance (Cl) of 4.1±0.5 mL/min/kg and a systemic volume of distribution (Vss) of 514±243 mL/kg. The Cl of the DNA was reduced more than 4-fold to 0.95±0.05 mL/min/kg when the DNA was incorporated in the interior of pegylated liposomes carrying no OX26 MAb (FIG. 2, left panel). The systemic clearance increased to 2.3±0.2 mL/min/kg when the OX26 MAb was tethered to the tip of the PEG tail of the liposome. The tissue uptake in brain, liver, kidney, and heart was also measured. These data show that attachment of the OX26 MAb to the tip of the pegylated liposome carrying the DNA exerted minor increases in tissue uptake in kidney or heart, moderate increases in liver, and a marked increase in the brain uptake of the pegylated immunoliposome (FIG. 3).

Figure 3:
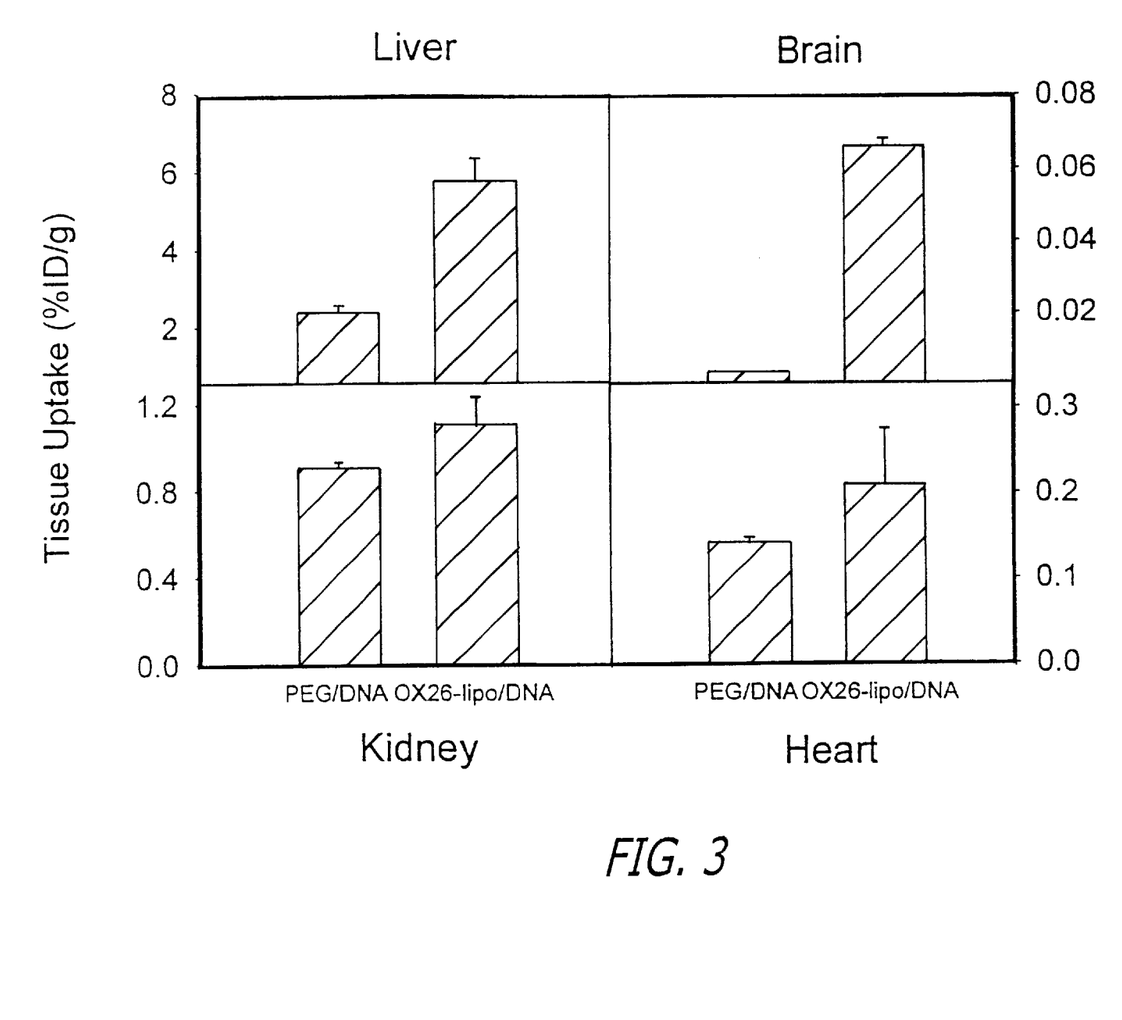
FIG. 3 depicts graphs in which the tissue uptake, expressed as % injected dose (ID) per gram tissue for liver, brain, kidney, or heart is shown at 120 minutes after intravenous injection of the encapsulated $^{32}PGL2$ plasmid DNA incorporated in either pegylated liposomes without antibody attached (PEG/DNA) or within the OX26 pegylated immunoliposomes (OX26-Lipo/DNA). Data are mean ±SE (n=3 rats/group).

The pegylated liposome carrying the plasmid DNA that had no OX26 tethered to the PEG strand was not significantly taken up by brain (FIG. 3). However, the OX26 pegylated liposome carrying the plasmid DNA was taken up by brain at a level of 0.066±0.002% ID/g brain at 120 minutes after intravenous injection (FIG. 3). This level of brain uptake is comparable to that of a neuroactive small molecule such as morphine, which has a brain uptake of 0.081±0.001% ID/g brain at 60 minutes after injection in the anesthetized rat (24).

The luciferase gene expression in brain and peripheral tissues was examined in a group of rats administered 10 µg of plasmid DNA per rat, which was incorporated in the interior of OX26 pegylated immunoliposomes. Organ luciferase enzyme activity, expressed as relative light units (RLU) per mg tissue protein, was measured at 24, 48, and 72 hours after intravenous injection. Although there was minimal targeting of the luciferous gene in the heart or kidney, the luciferase gene expression in brain was comparable to that of lung or spleen and peaked at 48 hours after intravenous administration (FIG. 4). The peak luciferase gene expression in liver was approximately 6-fold higher in that organ relative to brain, owing to the abundant expression of transferrin receptor on hepatocyte plasma membranes. For control studies, pegylated immunoliposomes were prepared except mouse $IgG_{2a}$, which is the same isotype as OX26, was conjugated to the pegylated liposomes in lieu of the OX26 MAb. The mouse $IgG_{2a}$ pegylated immunoliposome/pGL2 DNA complex was intravenously injected in anesthetized rats; the dose of pGL2 plasmid DNA was 10 µg per rat, or 40 µg. However, there was no measurable luciferase expression in brain or in any of the other organs at 48 hours after intravenous administration. This control experiment was repeated 3 times, and the luciferase activity was below the limits of detection in all samples.

The β-galactosidase histochemistry is shown in FIG. 5. The brain expresses β-galactosidase gene widely as seen at low magnification (FIG. 5A), whereas no β-galactosidase activity is observed in the control brain (FIG. 5B). Pyramidal neurons of the CA1–CA3 sectors of the hippocampus are clearly visualized as are the choroid plexi in both lateral ventricles; the choroid plexus is also positive for gene expression in both the dorsal horn and the mamillary recess of the third ventricle (FIG. 5A). The paired supraoptic nuclei of the hypothalamus at the base of the brain are viewed at low magnification (FIG. 5A). At higher magnification, the microvasculature (FIG. 5C), the choroid plexus epithelium (FIG. 5D), and thalamic nuclei (FIG. 5E) showed abundant β-galactosidase gene expression. Lower levels of gene expression in neurons throughout the brain were also visualized. Gene expression was detected histochemically throughout the liver in a peri-portal pattern, and gene expression was localized to hepatocytes, as shown in FIG. 5F. The high magnification view shows a puntate deposition of enzyme product throughout the liver cell, which suggests the enzyme is localized to the tubulovesicular network of the endoplasmic reticulum.

The above examples of practice demonstrate in accordance with the present invention that it is possible to achieve widespread expression of an exogenous gene in the brain following non-invasive intravenous administration. Replacement of the SV40 promoter and 3-untranslated region (UTR) parts of the plasmid with tissue- and gene-specific promoters and 3-UTR elements should enable region- and even cell-specific gene expression in the brain. This approach to gene therapy is well-suited for use in humans by simply changing the MAb moiety of the formulation (FIG. 1A) to the human insulin receptor (HIR) MAb (33) which is nearly 10 times more active in primates than is the anti-TfRMAb (5). Chimeric forms of the HIRMAb have been recently described, and the genetically engineered chimeric HIRMAb has identical transport properties at the primate or human BBB as does the original murine antibody (34).

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

Bibliography

1. Culver, K. W., Ram, Z., Wallbridge, S., Ishii, H., Oldfield, E. H., and Blaese, R. M. (1992) *Science* 256, 1550–1552.
2. Suhr, S. T. and Gage, F. H. (1993) *Arch Neurol.* 50, 1252–1268.
3. Martin, J. B. (1995) *Trends Biotechnol.* 13, 28–35.
4. Nilaver, G., Muldoon, L. L., Kroll, R. A., Pagel, M. A., Breakefield, X. O., Davidson, B. L., and Neuwelt, E. A. (1995) *Proc. Natl. Acad. Sci. USA* 92, 9829–9833.
5. Pardridge, W. M. (1997) *J. Cereb. Blood Flow. Metabol.* 17, 713–731.
6. Reimer, D. L., Zhang, Y., Kong, S., Wheeler, J. J., Graham, R. W., and Bally, M. B. (1995) *Biochem* 34, 12877–12883.
7. Matsui, H., Johnson, L. G., Randell, S. H. and Boucher, R. C. (1997) *J. Biol. Chem.* 272, 1117–1126.
8. Mahato, R. I., Rolland, A., and Tomlinson, E. (1997) *Pharm. Res.* 14, 853–859.
9. Huang, L. and Li, S. (1997) *Nature Biotech.* 15, 620–621.
10. Niidome, T., Ohmori, N., Ichinose, A., Wada, A., Mihara, H., Hirayama, T., and Aoyahi, H. (1997) *J. Biol. Chem.* 272, 15307–15312.
11. Plank, C., Tang, M. X., Wolfe, A. R., and Szoka, F. C. (1999) *Human Gene Therapy* 10, 319–332.
12. Osaka, G., Carey, K., Cuthbertson, A., Godowski, P., Patapoff, T., Ryan, A., Gadek, T., and Mordenti, J. (1996) *J. Pharm. Sci* 85, 612–618.
13. Holland, H. E. J., Nagy, D., Liu, J.-J., Spratt, K., Lee, Y. L., Danos, O., and Sullivan, S. M. (1997) *Pharm. Res.* 14, 742–749.
14. Song, Y. K., Liu, F., Chu, S., and Liu, D. (1997) *Human Gene Therapy* 8, 1585–1594.
15. Wu, G. Y. and Wu, C. H. (1987) *J. Biol. Chem.* 262, 4429–4432.
16. Chowdhury, N. R., Wu, C. H., Wu, G. Y., Yemeni, P. C., Bommineni, V. R., and Chowdhury, J. R. (1993) *J. Biol. Chem.* 268, 11265–11271.
17. Perales, J. C., Grossmann, G. A., Molas, M., Liu, G., Ferkol, T., Harpst, J., Oda, H., and Hanson, R. W. (1997) *J. Biol Chem.* 272, 7398–7407.
18. Pardridge, W. M., Triguero, D., and Buciak, J. B. (1989) *J. Pharmacol. Exp. Ther.* 251, 821–826.
19. Huwyler, J., Wu, D., and Pardridge, W. M. (1996) *Proc. Natl. Acad. Sci. USA* 93, 14164–14169.
20. Monnard, P. A., Oberholzer, T., and Luisi, P. (1997) *Biochem. Biophys. Acta* 1329, 39–50.
21. Kang, Y.-S. and Pardridge, W. M. (1994) *J. Pharmacol. Exp. Ther.* 269, 344–350.
22. Pardridge, W. M., Buciak, J. L., and Yoshikawa, T. (1992) *J. Pharmacol. Exp. Ther.* 261, 1175–1180.
23. Dwyer, K. J., Boado, R. J., and Pardridge, W. M. (1996) *J. Neurochem.* 66, 449–458.
24. Wu, D., Kang, Y.-S., Bickel, U., and Pardridge, W. M. (1997) *Drug Metab. Disp.* 25, 768–771.
25. Wood, M. J. A., Charlton, H. M., Wood, K. J., Kajiwara, K., and Byrnes, A. P. (1996) *Trends Neurosci.* 19, 497–501.
26. Hong, K., Zheng, W., Baker, A., and Papahadjopoulos, D. (1997) *FEBS Lett.* 400, 233–237.
27. Mounkes, L. C., Zhong, W., Ciperes-Palacin, G., Heath, T. D., and Debs, R. J. (1998) *J. Biol. Chem.* 273, 26164–26170.
28. Lee, H. J., Engelhardt, B., Lesley, J., Bickel, U., and Pardridge, W. M. (2000) *J. Pharmacol. Exp. Ther.* 292, 1048–1052.
29. Barron, L. G., Uyechi, L. S., and Szoka, F. C. (1999) *Gene Therapy* 6, 1179–1183.
30. Zhu, N., Liggitt, D., Liu, Y., and Debs, R. (1993) *Science* 261, 209–212.
31. Huwyler, J. and Pardridge, W. M. (1998) *J. Neurochem.* 70, 883–886.
32. Mash, D. C., Pablo, J., Flynn, D. D., Efange, S. M. and Weinger, W. J. (1990) *J. Neurochem.* 55, 1972–1979.
33. Pardridge, W. M., Kang, Y.-S., Buciak, J. L., and Yang, J. (1995) *Pharm Res.,* 12, 807–816.
34. Coloma, M. J., Lee, H. J., Kurihara, A., Landaw, E. M., Boado, R. J., Morrison, S. L., and Pardridge, W. M. (2000) *Pharm Res.,* 17, 266–264
35. Beisiegel, U., Schneider, W. J., Goldstein, J. L., Anderson, R. G. W., and Brown, M. S. (1981) *J. Biol. Chem.* 256, 11923–11931.
36. Shechter, Y., Maron, R., Elias, D., and Cohen, I. R. (1982) *Science* 216, 542–545.
37. Soos, M. A. et al. (1989) *Proc. Natl. Acad. Sci, USA,* 86, 5217–5221.
38. Domingo, D. L. and Trowbridge, I. S. (1985) *Methods in Enzymol.* 112, 238–247.

What is claimed is:

1. A receptor-specific liposome for delivering a gene across the blood brain barrier and the brain cell membrane, said liposome comprising:
   a liposome having an exterior surface and an internal compartment;
   a gene comprising a sufficient amount of genetic information to encode an agent, said gene being located within the internal compartment of said liposome;
   a plurality of blood brain barrier and brain cell membrane targeting agents; and
   a plurality of conjugation agents wherein each targeting agent is connected to the exterior surface of said liposome via at least one of said conjugation agents.

2. A receptor-specific liposome according to claim 1 wherein said liposome exterior surface defines a sphere having a diameter of less than 200 nanometers.

3. A receptor-specific liposome according to claim 1 wherein said gene encodes a therapeutic agent selected from the group consisting of genes encoding brain-derived neurotrophic factor, tyrosine hydroxylase, aromatic amino acid decarboxylase, β-glucoronidase, hexosaminidase A, thymidine kinase, and genes encoding for antisense RNA.

4. A receptor-specific liposome according to claim 1 wherein said gene is located within a plasmid.

5. A receptor-specific liposome according to claim 1 wherein the molecular weight of said gene is above 30,000 Daltons or wherein said gene comprises at least 100 nucleotides.

6. A receptor-specific liposome according to claim 1 wherein between 5 and 1000 blood brain barrier or brain cell membrane targeting agents are conjugated to the surface of said liposome.

7. A receptor-specific liposome according to claim 1 wherein between 25 and 40 blood brain barrier or brain cell membrane targeting agents are conjugated to the surface of said liposome.

8. A receptor-specific liposome according to claim 1 wherein said conjugation agent is selected from the group consisting of polyethylene glycol, sphingomyelin and organic polymers.

9. A receptor-specific liposome according to claim 1 wherein the molecular weight of said conjugation agent is between 1000 and 50,000 Daltons.

10. A receptor-specific liposome according to claim 1 wherein said blood-brain barrier and brain cell membrane targeting agent is selected from the group consisting of insulin, transferrin, insulin-like growth factor (IGF), leptin, low density lipoprotein (LDL), and the corresponding peptidomimetic monoclonal antibodies that mimic these endogenous peptides and bind to the insulin, transferrin, IGF, leptin, or LDL receptor on the blood-brain barrier and brain cell membrane.

11. A method for delivering a gene across the blood brain barrier for expression in the brain, said method comprising the steps of administering to an animal an effective amount of a preparation comprising:
   a) a receptor-specific liposome comprising:
      a liposome having an exterior surface and an internal compartment;
      a gene comprising a sufficient amount of genetic information to encode a pharmaceutical agent, said gene being located within the internal compartment of said liposome;
      a plurality of blood brain barrier and brain cell membrane targeting agents;
      a plurality of conjugation agents wherein each targeting agent is connected to the exterior surface of said liposome via at least one of said conjugation agents; and
   b) a pharmaceutically acceptable carrier for said receptor-specific liposome,
wherein said receptor-specific liposome crosses said blood brain barrier to provide expression of said gene in said brain.

12. A method according to claim 11 wherein said preparation is administered intravenously.

13. A method according to claim 11 wherein said liposome exterior surface defines a sphere having a diameter of less than 200 nanometers.

14. A method according to claim 11 wherein said gene encodes a therapeutic agent selected from the group consisting of genes encoding brain-derived neurotrophic factor, tyrosine hydroxylase, aromatic amino acid decarboxylase, glucuronidase, hexosaminidase A, thymidine kinase and genes encoding for antisense RNA.

15. A method according to claim 11 wherein said gene is located within a plasmid.

16. A method according to claim 11 wherein said gene comprises at least 100 nucleotides.

17. A method according to claim 11 wherein between 5 and 1000 blood brain barrier and brain cell membrane targeting agents are conjugated to the surface of said liposome.

18. A method according to claim 11 wherein said conjugation agent is selected from the group consisting of polyethylene glycol, sphingomyelin, and other organic polymeric substances.

19. A method according to claim 11 wherein said blood-brain barrier or brain cell membrane targeting agent is selected from the group consisting of insulin, transferrin, insulin-like growth factor (IGF), leptin, low density lipoprotein (LDL), and the corresponding peptidomimetic monoclonal antibodies that mimic these endogenous peptides and bind to the insulin, transferrin, IGF, leptin, or LDL receptor on the blood-brain barrier and brain cell membrane.

20. A method according to claim 17 wherein between 25 and 40 blood brain barrier and brain cell membrane targeting agents are conjugated to the surface of said liposome.

21. A method according to claim 18 wherein the molecular weight of said conjugation agent is between 1000 and 50,000 Daltons.

22. A composition comprising:
   a) a receptor-specific liposome comprising:
      a liposome having an exterior surface and an internal compartment;
      a gene comprising a sufficient amount of genetic information to encode an agent, said gene being located within the internal compartment of said liposome;
      a plurality of blood brain barrier targeting agents;
      a plurality of conjugation agents wherein each targeting agent is connected to the exterior surface of said liposome via at least one of said conjugation agents; and
   b) a pharmaceutically acceptable carrier for said receptor-specific liposome.

23. A receptor-specific nanocontainer for delivering a gene to a cell having a specific receptor, said receptor-specific nanocontainer comprising:
   a nanocontainer having an exterior surface and an internal compartment;
   a gene comprising a sufficient amount of genetic information to encode a pharmaceutical agent, said gene being located within the internal compartment of said nanocontainer;
   a plurality of receptor-specific targeting agents which are capable of targeting the receptor located on said cell; and
   a plurality of conjugation agents wherein each targeting agent is connected to the exterior surface of said nanocontainer via at least one of said conjugation agents.

24. A receptor-specific nanocontainer according to claim 23 wherein said cell having said specific receptor is selected from the group of cells consisting of brain, liver, lung and spleen.

25. A method for delivering a gene to a cell having a specific receptor, said method comprising the step of administering to an animal an effective amount of a preparation comprising:
   a) a receptor-specific nanocontainer comprising:
      a nanocontainer having an exterior surface and an internal compartment;
      a gene comprising a sufficient amount of genetic information to encode a pharmaceutical agent, said gene being located within the internal compartment of said nanocontainer;
      a plurality of receptor-specific targeting agents which are capable of targeting the receptor located on said cell; and
      a plurality of conjugation agents wherein each targeting agent is connected to the exterior surface of said nanocontainer via at least one of said conjugation agents; and
   b) a pharmaceutically acceptable carrier for said receptor-specific nanocontainer,
wherein said receptor-specific nanocontainer is delivered to said cell having having a specific receptor.

26. A method according to claim 25 wherein the cells to which said nanocontainer is targeted are selected from the group of cells consisting of brain, liver, lung and spleen cells.

* * * * *